United States Patent [19]

Wermuth et al.

[11] Patent Number: 4,710,499
[45] Date of Patent: Dec. 1, 1987

[54] NEW DERIVATIVES OF PYRIDAZINE ACTIVE ON THE CENTRAL NERVOUS SYSTEM

[75] Inventors: Camille G. Wermuth, Strasbourg; Jean-Pierre Chambon, Montarnaud, both of France

[73] Assignee: Sanofi, Paris, France

[21] Appl. No.: 638,363

[22] Filed: Aug. 7, 1984

Related U.S. Application Data

[63] Continuation of Ser. No. 406,042, Aug. 6, 1982, abandoned.

[30] Foreign Application Priority Data

Aug. 11, 1981 [FR] France .................. 81 15546

[51] Int. Cl.$^4$ .................. C07D 237/20; A61K 31/50
[52] U.S. Cl. .................. 514/247; 544/224; 544/237
[58] Field of Search .............. 424/250; 544/224, 237; 514/247

[56] References Cited

U.S. PATENT DOCUMENTS 4,353,903 10/1982 Fabiani et al. .................. 544/224

FOREIGN PATENT DOCUMENTS 2229215 1/1973 Fed. Rep. of Germany .

*Primary Examiner*—Donald G. Daus
*Assistant Examiner*—William A. Teoli, Jr.
*Attorney, Agent, or Firm*—Scully, Scott, Murphy & Presser

[57] ABSTRACT

The present invention relates to derivatives of pyridazine of formula:

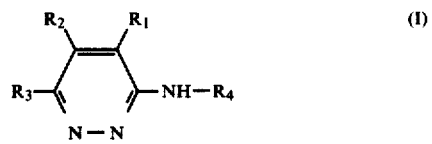

in which $R_1$ is alkyl or a phenyl group and $R_2$ is H or $R_1$ and $R_2$ form, with the carbon atoms to which they are attached, a benzene cycle, $R_3$ is H or phenyl and $R_4$ is

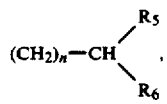

in which $R_5$ is H or $CH_3$ and $R_6$ is H, OH, OR or OCOR; it also relates to a process for preparing the products of formula (I) and to the drugs containing at least one of said products.

20 Claims, No Drawings

NEW DERIVATIVES OF PYRIDAZINE ACTIVE ON THE CENTRAL NERVOUS SYSTEM

This is a continuation of copending application Ser. No. 406,042, filed on Aug. 6, 1982, now abandoned.

For numerous years, derivatives of pyridazine have been proposed as drugs. In a large number of cases, these are substances active on the cardiovascular system, presenting in particular an antihypertensive or vasodilator effect. More rarely, an anti-inflammatory and analgesic action has been mentioned among pyridazine derivatives. Finally, French Pat. No. 2 141 697 describes a family of products of general formula:

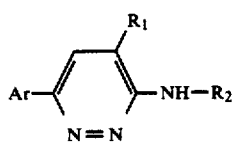

where
R$_1$ represents hydrogen or a lower alkyl group
Ar represents an aromatic radical
R$_2$ designates a group

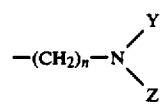

in which n=2 or 3 and Y and Z represent a lower alkyl group or

constitutes a heterocyclic radical.

These compounds are characterised by a psychotherapeutic action of psychotonic type.

A subsequent study of the compound where R$_1$=CH$_3$, Ar=phenyl and

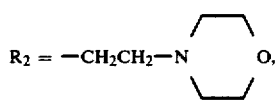

which has received the International Common Denomination "Minaprine", has shown that it is question of a psychotherapeutic action of a new type which has been designated by "disinhibitory" activity. Furthermore, at a dose greater than 100 mg/kg per os, this product shows itself to be convulsivant.

It has now been discovered that by modifying the nature of the substituent R$_2$, the activity of the compounds obtained can be surprizingly considerably modified, to become anti-convulsivant.

The present invention relates to a family of derivatives of pyridazine of general formula:

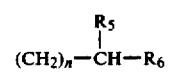

in which:
R$_1$ represents a lower alkyl group and in particular the methyl group, or a phenyl group;
R$_2$ represents hydrogen, or
R$_1$ and R$_2$ together constitute a group: —CH=CH—CH=CH— so as to constitute a benzene cycle attached to the pyridazine ring;
R$_3$ represents hydrogen or a phenyl;
R$_4$ represents a group $$(CH_2)_n-\overset{R_5}{\underset{|}{CH}}-R_6$$

in which n is an integer which may vary from 0 to 7;
R$_5$ represents hydrogen or a methyl group;
R$_6$ represents hydrogen, a hydroxyl group, an ether group OR$_7$, an ester group OCOR$_7$ in which R$_7$ represents a lower alkyl group (1 to 4 carbon atoms).

The present invention also relates to the acid addition salts of the compounds of formula (I). It also comprises a process for preparing the compounds of formula (I) as well as the application thereto in therapeutics.

Compounds (I) are obtained from a suitably substituted 3-chloro pyridazine (1) according to the reaction scheme:

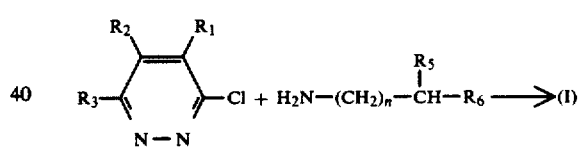

Reaction between the chlorinated derivative 1 and the amine 2 is generally carried out by heating within a suitable solvent, such as an alcohol, most often at boiling temperature of the solvent. The duration of the reaction varies from a few hours to several days depending on the nature of the reagents employed. When the reaction proves to be too slow, it may be catalyzed by addition of a small quantity of powdered copper.

The reaction is carried out in the presence of a hydracid acceptor intended to fix the hydrochloric acid formed in the reaction. An excess of the amine 2 is most often used as such.

Isolation of the compound (I) is effected by taking up in water and extraction by a suitable solvent such as ethyl acetate.

Compounds (I) thus obtained may be salified in conventional manner by action of the acid on a hot solution of the base, the solvent being selected so that the salt crystallizes by cooling.

When R$_6$ represents a group OCOR$_7$, a variant of the process consists in preparing the corresponding compound (I) where R$_6$ represents OH then in acylating the latter according to a conventional process for example by action of the chloride of acid $R_7COCl$ within the pyridine.

The following non-limiting examples are given by way of illustration of the present invention.

EXAMPLE 1

3-BUTYLAMINO 4-METHYL 6-PHENYL PYRIDAZINE (TARTRATE) (CM 30434)

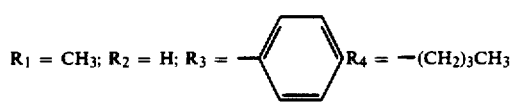

(I)

$R_1 = CH_3; R_2 = H; R_3 = $ phenyl; $R_4 = -(CH_2)_3CH_3$

The mixture of 10.3 g of 3-chloro 4-methyl 6-phenyl pyridazine and 7.5 g of butylamine in 100 ml of butanol is taken to reflux for 48 hours. The mixture is poured into 200 ml of water and extracted with ethyl acetate. The organic phase is separated and extracted with a 5N aqueous solution of sulfuric acid. The acid extract is rendered alkaline by addition of sodium bicarbonate then extracted with chloroform. The solution is washed with water, dried and the solvent is evaporated. An oily product is obtained. This oil is dissolved in hot isopropanol, an equivalent of tartric acid is added and the product is heated up to dissolution. After cooling, a colourless solid is drained which is recrystallized in isopropanol; m.p.: 184°–6° C.; Yield 12.5 g.

The tartrate crystallizes with 2 molecules of water.

By operating in the same manner, but by replacing the butylamine by an equivalent quantity of octylamine, the tartrate of 3-octylamino 4-methyl 6-phenyl pyridazine (CM 30435) is obtained; m.p.: 164°–6° C. (isopropanol-ether); Yield 54%.

EXAMPLE 2

3-(2-HYDROXY ETHYLAMINO)4-METHYL 6-PHENYL PYRIDAZINE (HYDROCHLORIDE) (CM 30094)

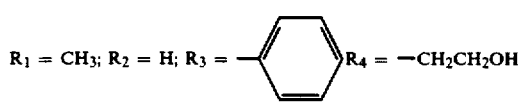

(I)

$R_1 = CH_3; R_2 = H; R_3 = $ phenyl; $R_4 = -CH_2CH_2OH$

The mixture of 30.6 g of 3-chloro 4-methyl 6-phenyl pyridazine, 36.6 g of 2-amino ethanol and 0.1 g of powdered copper in 400 ml of butanol is taken to reflux for 3 days.

The mixture is poured into 500 ml of water and the solution is filtered over a Büchner funnel. The product is extracted with ethyl acetate and the solution is dried over magnesium sulfate. The solvent is evaporated to dryness. The residue crystallizes. Recrystallization takes place in a 2-1 (vol/vol) mixture of ethyl acetate-isopropanol. Colourless crystals are obtained (20 g); m.p.: 151° C.

Hydrochloride: 11.45 g of base is dissolved in 100 ml of isopropanol, with heating up to dissolution. 4.7 ml of concentrated hydrochloric acid are added and the product is left to crystallize by cooling. Recrystallization is carried out twice in methanol.

A colourless solid is obtained (7 g); m.p.: 200° C.

EXAMPLES 3 TO 6

By varying the aminoalcohol or the chlorinated derivative used, the compounds (I) shown in Table I are obtained.

TABLE I

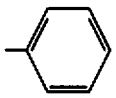

| Code No. CM | $R_1$ | n | $R_5$ | $R_6$ | Duration of the reaction in hours | Base Melting point °C. (solvent) | Hydrochloride Melting point °C. (solvent) |
| --- | --- | --- | --- | --- | --- | --- | --- |
| 30 095 | —$CH_3$ | 2 | H | OH | 72 | 134 (isopropanol) | 209 (ethanol 95) |
| 30 096 | —$CH_3$ | 1 | $CH_3$ | OH | 72 | 114 (ethyl acetate) | 193 (ethanol at 95) |
| 30 097 | —$CH_3$ | 3 | H | OH | 72 | 93 (ethyl acetate) | 196 (ethanol at 95) |
| 30 339 | cyclohexyl | 1 | H | OH | 48 | hygroscopic solid | 182 (isopropanol) |

EXAMPLE 7

3-(2-PROPIONYLOXY ETHYLAMINO)4-METHYL 6-PHENYL PYRIDAZINE (MALATE) (CM 30098)

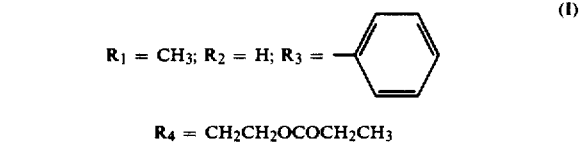

(I)

$R_1 = CH_3; R_2 = H; R_3 = $ phenyl $R_4 = CH_2CH_2OCOCH_2CH_3$ 16 g of compound CM 30094, base obtained in Example 2, are dissolved in 250 ml of pyridine by stirring at ambient temperature. 6.3 ml of propionyl chloride are then added, drop by drop, stirring being continued. At the end of the addition, stirring is continued for 2 hours at ambient temperature, the product then being evaporated to dryness. The residue dissolved in the minimum of chloroform is chromatographed over a silica column. By eluting with a 50-50 (vol/vol) mixture of ethyl acetate-hexane, a colourless solid is obtained after evaporation.

After recrystallization in a small volume of ethyl acetate: m.p. 102° C.; weight: 8 g.

Malate: 8 g of base are dissolved in 100 ml of hot isopropanol then the hot solution of 4.02 g of malic acid is added in 10 ml of isopropanol. After cooling and addition of a little ether anhydride, a colourless solid is isolated which is recrystallized twice in acetonitrile. m.p.: 110° C.; weight: 6.5 g.

In the same way, by replacing the propionyl chloride by an equivalent quantity of acetyl chloride, the 3-(2-acetoxy ethylamino)4-methyl 6-phenyl pyridazine is isolated by the same treatment. m.p. 127° C.

Malate m.p.: 102°-5° C. (acetonitrile).

EXAMPLE 8

3-(2-METHOXY ETHYLAMINO)4-METHYL 6-PHENYL PYRIDAZINE (HYDROCHLORIDE) (CM 30310)

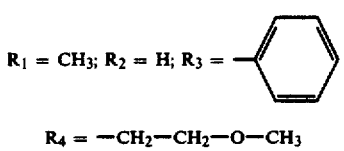

(I) $R_1 = CH_3$; $R_2 = H$; $R_3 = $ $R_4 = -CH_2-CH_2-O-CH_3$

A mixture of 7 g of 3-chloro 4-methyl 6-phenyl pyridazine and 7 g of 2-methoxy ethylamine in 50 ml of butanol is taken to reflux for 4 days. The hot solution is poured into 200 ml of water and extracted with ethyl acetate. The organic solution is dried over magnesium sulfate then evaporated to dryness.

The residue is distilled under high vacuum Eb/0.1 mm; m.p. 208°-210° C.; weight: 6.8 g.

Hydrochloride: 6.8 g of the base are dissolved in hot isopropanol then 2.5 ml of concentrated hydrochloric acid are added and the product left to crystallize. m.p. 194° C.; weight: 6.5 g. Crystallizes with ½ molecule of water.

By operating similarly from 3-chloro 4,6-diphenyl pyridazine, the 3-(2-methoxy ethylamino)4,6-diphenyl pyridazine (CM 30340) is obtained in the same manner. Base m.p.: 92° C. (isopropyl ether) Hydrochloride m.p.: 193° C. (isopropanol).

EXAMPLE 9

3-(2-METHOXY ETHYLAMINO)PHTHALAZINE (HYDROCHLORIDE) (CM 30320)

(I) $R_1$ and $R_2 = -CH=CH-CH=CH-$; $R_3 = H$
$R_4 = -CH_2CH_2OCH_3$

A mixture of 10 g of 3-chloro phthalazine and 80 g of 2-methoxy ethylamine in 80 ml ethanol is heated to reflux for 1 hour.

The solvent is evaporated and the residue is poured into 500 ml of water. The product is rendered alkaline by concentrated sodium hydroxide and extracted with ethyl acetate. The organic phase is separated, dried and the solvent is evaporated to dryness. The residue crystallizes and it is recrystallized in a 50-50 (vol/vol) mixture of isopropanol-isopropyl ether.

Pale yellow crystals are obtained (10 g); m.p.: 131° C.

Hydrochloride: 5 g of base are dissolved in the isopropanol and 2.6 ml of concentrated hydrochloric acid are added. The solid is drained and recrystallized in isopropanol; weight: 5 g; m.p.: 170° C. The hydrochloride crystallizes with 1 molecule of water.

The products according to the invention have been studied as far as their pharmacological activity is concerned.

ANTICONVULSIVANT ACTIVITY

The anticonvulsivant activity of the derivatives was assessed with respect to two chemical agents: strychnine and bicuculline, and with respect to electric shock. In these various tests, the products were compared with the minaprine described in French Patent 2 141 697 mentioned hereinabove.

The products were also compared with the sodium salt of valproic acid (DCI) of which the anticonvulsivant activity is well known and used in human therapeutics.

Anti-Strychnine Activity

The products are administered by the oral route 30 minutes before the strychnine 0.9 mg/kg i.p.. The occurrence of tetanic crises as well as mortality are noted during the 60 minutes following administration of strychnine.

Anti-Bicuculline Activity

The products are administered by the oral route 30 minutes before the bicuculline 0.9 mg/kg i.v.. The occurrence of clonic, tonic crises as well as mortality are noted during the 60 minutes following administration of bicuculline.

Anti-Electric Shock Activity

The products were administered per os 30 minutes before the electric shock (12.5 volts for 0.5 seconds). The electric shock was given to the animal via corneal electrodes. The occurrence of clinico-tonic convulsions in the control animals was immediate. The animals not presenting extension of the rear limbs were considered as protected.

In the three cases, the products are administered in a range of doses to batches of 10 mice per dose.

For each product, the effective dose 50 (ED 50) or dose which antagonises the convulsivant effect of the agent used in 50% of the animals treated, is determined.

Table III shows the results obtained with various products representative of the invention.

The products of the invention manifest a considerable anti-convulsivant activity. With respect to strychnine, this activity is particularly powerful for compounds CM 30096, 30310 and 30339. With respect to bibuculline and electric shock, the anti-convulsivant activity is slightly less powerful but is still considerable, particularly for the derivatives CM 30096 and 30370.

As far as the reference products are concerned, the minaprine is totally inactive in these tests up to the maximum dose tolerated. As to the sodium valproate administered by the oral route, it presents, under the same experimental conditions, a effective dose 50 most often greater than that of the products of the invention.

TABLE II

| | Inhibition of the convulsivant effects of | | |
|---|---|---|---|
| Products | Strychinine $ED_{50}$ (mg/kg) | Bicuculline $ED_{50}$ (mg/kg) | electric shock $ED_{50}$ (mg/kg) |
| CM 30094 | 119 | 286 | 107 |
| CM 30096 | 92 | 175 | 209 |
| CM 30310 | 158 | 136 | 78 |
| CM 30339 | 145 | 86 | ~200 |
| Minaprine | Inactive | Inactive | Inactive |
| Sodium Valproate | 480 | 234 | 290 |

ACUTE TOXICITY

The products to be studied were administered by the oral route at doses of 250, 500 and 1000 mg/kg to batches of 5 mice. The mortality provoked by the derivatives was assessed during the 24 hours following administration of the product.

TABLE III

| N° Product | p. cent of mortality | | |
|---|---|---|---|
| | at 1000 mg/kg | at 500 mg/kg | at 250 mg/kg |
| Minaprine | 100 | 100 | 100 |
| CM 30 094 | 0 | 0 | 0 |
| CM 30 096 | 100 | 20 | 0 |
| CM 30 097 | 100 | 0 | 0 |
| CM 30 310 | 100 | 0 | 0 |
| CM 30 320 | 100 | 80 | 0 |
| CM 30 339 | 60 | 60 | 0 |
| CM 30 340 | 20 | 0 | 0 |
| CM 30 434 | 0 | 0 | 0 |
| CM 30 451 | 0 | 0 | 0 |
| CM 30 462 | 40 | 20 | 0 |

The results expressed in percentage of animals which die after administration of various products of the invention are noted in the above Table. All the products studied presented no toxicity at the dose of 250 mg/kg p.os. At the dose of 500 mg/kg p.os, only derivatives CM 30096, CM 30320, CM 30339 and CM 30462 have a toxic effect. The minaprine has a much greater toxic effect, it provokes 20% of mortality from the dose of 100 mg/kg p.os in the mouse.

The tests thus carried out show that the products according to the invention present interesting pharmacological properties and low toxicity. Consequently, they may be used in human therapeutics, particularly for the treatment of psychic, neurological or neuromuscular disorders.

In particular, the products according to the invention may be used for the treatment of disorders in mood or behaviour: nervosity, irritability and for the treatment of anxious states and insomnia.

These products may be administered by the oral route or injectable route. The pharmaceutical compositions may be solid or liquid and be for example in the form of tablets, capsules, granulates, suppositories or injectable preparations.

Dosage may vary to large proportions, particularly depending on the type and seriousness of the disorder to be treated and depending on the mode of administration. Most often in the adult, by the oral route, it is between 0.050 and 0.500 g per day possibly distributed in several doses.

By way of example, the following Galenic preparations may be indicated:

| Tablets | |
|---|---|
| CM 30310 | 200 mg |
| Microcrystalline cellulose | 100 mg |
| Lactose | 197 mg |
| Magnesium stearate | 3 mg |
| | 500 mg |

What is claimed is:
1. Pyridazine compounds having the formula:

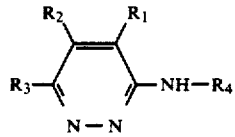

in which
  $R_1$ is a lower alkyl having 1 to 4 carbon atoms or a phenyl group;
  $R_2$ represents H;
  $R_3$ represents H or phenyl;
  $R_4$ represents a group

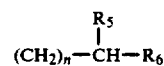

in which n is an integer of from 1 to 7, $R_5$ is H or $CH_3$ and $R_6$ is selected from H, $OR_7$, an ester group $OCOR_7$ in which $R_7$ represents a lower alkyl radical having 1 to 4 carbon atoms as well as the pharmaceutically acceptable acid addition salts of said compounds.

2. Pyridazine compounds as in claim 1 in which $R_6$ is $OR_7$.

3. Pyridazine compounds as in claim 1 in which $R_6$ is $OCOR_7$.

4. Pyridazine compounds as in claim 1 in which n is 2.

5. Pyridazine compounds as in claim 1 in which n is 3.

6. Pyridazine compounds as in claim 5 in which $R_6$ is H.

7. A composition for the treatment of convulsive disorders in mammals comprising, as active agent for treating said disorders, an effective amount of a pyridazine compound having the formula:

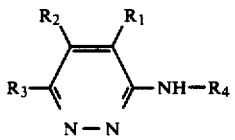

in which
  $R_1$ is a lower alkyl having 1 to 4 carbon atoms or a phenyl group;
  $R_2$ represents H;
  $R_3$ represents H or phenyl;
  $R_4$ represents a group

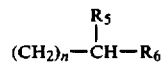

in which n is an integer of from 1 to 7, $R_5$ is H or $CH_3$ and $R_6$ is selected from H, OH, $OR_7$, an ester group $OCOR_7$ in which $R_7$ represents a lower alkyl radical having 1 to 4 carbon atoms, or an acid addition salt of said compound, and a pharmaceutically acceptable carrier for said compound.

8. A composition as in claim 7 in which $R_1$ or $R_3$ is phenyl.

9. A composition as in claim 7 in which $R_1$ is methyl.

10. A composition as in claim 9 in which $R_3$ is phenyl.

11. A composition as in claim 10 in which $R_4$ is $(CH_2)_n$—$CH_2$—OH.

12. A composition as in claim 11 in which n is 1.

13. A composition as in claim 7 in which $R_1$ is phenyl.

14. A composition as in claim 13 in which $R_3$ is H.

15. A composition as in claim 14 in which $R_4$ is $(CH_2)_n-CH_2-OH$.

16. A composition as in claim 15 in which n is 1.

17. A composition as in claim 8 in which $R_4$ is $(CH_2)_n-CH_2-OH$.

18. A composition as in claim 17 in which n is 1.

19. A process for the treatment of a convulsive disorder in mammals which comprises employing an effective amount of a composition of claim 9 for said treatment.

20. A process as in claim 19 in which the composition of claim 19 is employed for said treatment.

* * * * *

UNITED STATES PATENT AND TRADEMARK OFFICE
CERTIFICATE OF CORRECTION

PATENT NO. : 4,710,499

DATED : December 1, 1987

INVENTOR(S) : Camille D. Wermuth, et al.

It is certified that error appears in the above-identified patent and that said Letters Patent is hereby corrected as shown below:

<u>IN THE CLAIMS:</u>

Claim 19, line 3: "9" should read as --7--

Claim 20, line 2: "19" should read as --17--

Signed and Sealed this

Fifth Day of July, 1988

Attest:

DONALD J. QUIGG

Attesting Officer     Commissioner of Patents and Trademarks